United States Patent [19]

Halbritter et al.

[11] Patent Number: 6,042,799
[45] Date of Patent: Mar. 28, 2000

[54] COPRODUCTION OF ACETYLENE AND HYDROCYANIC ACID FROM ACRYLONITRILE

[75] Inventors: Klaus Halbritter, Heidelberg; Michael Henningsen, Frankenthal; Manfred Julius, Limburgerhof; Wolf Stegmaier, Böhl-Iggelheim, all of Germany

[73] Assignee: BASF Aktiengesellschaft, Ludwigshafen, Germany

[21] Appl. No.: 09/034,274

[22] Filed: Mar. 4, 1998

[30] Foreign Application Priority Data

Mar. 6, 1997 [DE] Germany ............... 197 09 261

[51] Int. Cl.[7] ............... C01C 3/08; C07C 2/00; C07C 2/02
[52] U.S. Cl. ............... 423/372; 585/534; 585/538; 585/539
[58] Field of Search ............... 423/371, 372; 585/534, 539, 538

[56] References Cited

U.S. PATENT DOCUMENTS 3,607,962  9/1971  Krekeler ............... 585/325
4,136,156  1/1979  Weigert ............... 423/372
5,804,689  9/1998  Schodel et al. ............... 585/539

FOREIGN PATENT DOCUMENTS 1 668 102  6/1971  Germany.

OTHER PUBLICATIONS

Lifshitz et al. Pyrolysis of Acrylonitrile at Elevated Temperature, Studies with a Single–Pulse Shock Tube. Journal of Physical Chemistry, American Chemical Society, pp. 1369–1373, 1989.
Robert H. Perry and Cecil H. Chilton. Chemical Engineers' Handbook, Fifth Edition. pp. 4–2 to 4–43, 1973.
Ullmann's Ency. Fifth Ed., vol. A1 111–112.
Int. Jrl. Chem. Kinetics, vol. 19, 61–79, 1987.
Combustion and flame 78:43–57 (1989).
American Chem. Soc., Lifshitz et al., Pyrolysis of Acrylonitrile at Elevated Temperatures . . . .

*Primary Examiner*—Steven P. Griffin
*Assistant Examiner*—Maribel Medina
*Attorney, Agent, or Firm*—Keil & Weinkauf

[57] ABSTRACT

In the process for preparing acetylene and hydrocyanic acid by pyrolyzing acrylonitrile in a reactor, the gaseous reaction products of the pyrolysis are quenched down to less than 100° C. immediately, advantageously within seconds, preferably within ≦1 s, of leaving the pyrolysis zone.

10 Claims, No Drawings

COPRODUCTION OF ACETYLENE AND HYDROCYANIC ACID FROM ACRYLONITRILE

The present invention relates to a process for preparing acetylene and hydrocyanic acid; more particularly, the present invention relates to the coproduction of these two compounds.

Acetylene and hydrocyanic acid, the starting points for a multiplicity of basic and intermediate organics, are important synthetic building blocks in the chemical industry. One way to prepare acetylene, oxidative methane coupling, requires highly integrated sites, since only they can provide for sensible utilization of the reaction "by-products". For instance, in the aforementioned process for acetylene production (oil quench process), the by-products per metric ton of acetylene include 10600 m³ of crude synthesis gas, 13 t of steam and 0.3 t of carbon black (data from Ullmann's Encyclopedia of Industrial Chemistry, 5th ed.—1985, Vol. A1, p.112).

There is therefore great interest in processes providing alternative selective routes to acetylene with coproduction of hydrocyanic acid. A. Lifshitz et al. [Int. J. Chem. Kinet. 19 (1987) 61–79; Combustion and Flame 78 (1989) 43–57; J. Phys. Chem. 93 (1989) 1369–1373] investigated the pyrolysis of N-containing organic molecules using the single-pulse shock tube technique. Hydrocyanic acid and acetylene are each obtained with a selectivity of about 48% at 1425K starting from acrylonitrile (1% of $H_2C=CH-CN$ in argon) with a conversion of about 25%, ie. yields were only about 12% each. The single-pulse shock technique for decomposing acrylonitrile, however, is a batch method, which is completely unsuitable for economical coproduction of hydrocyanic acid and acetylene, since it cannot be practiced on a continuous chemical reactor. In addition, a temperature of at least 1450K (1177° C.) has to be employed to obtain an acrylonitrile conversion of 40%.

U.S. Pat. No. 4,136,156 discloses the formation of hydrocyanic acid in the thermolysis of organic nitriles, such as benzonitrile, at 400–700° C. in the presence of noble metal catalysts and hydrogen.

Furthermore, DE-A 16 68 102 discloses that it is possible to prepare acetylene by dehalogenation of dihaloethane or vinyl bromide (vinyl chloride) in the presence of basic catalysts, such as BaO.

It is an object of the present invention to develop a process whereby acrylonitrile is converted into acetylene and hydrocyanic acid at one and the same time. This process shall, in particular, be advantageously useful on an industrial scale as well.

We have found that this object is achieved by a process for preparing acetylene and hydrocyanic acid by pyrolyzing acrylonitrile in a reactor. The form of the reactor is of minor importance; advantageous reactors are reactors which are optionally packed with an inert material and in which a comparatively high temperature of the order of 1000° C. can be realized together with a short residence time, for the gas to be pyrolyzed, of 1 sec or fractions thereof—including especially a subsequent cooling phase. In terms of basic principle, such reactors are realized in acetylene burners, for example.

The present invention accordingly provides an acetylene and hydrocyanic acid production process for which the general equation

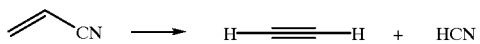

provides a description in terms of a pyrolytic dehydrocyanation of acrylonitrile.

The acrylonitrile pyrolysis of the present invention can be carried out in the presence of an inert gas, such as nitrogen or argon. In a preferred embodiment of the process of the present invention, the reaction can be carried out continuously in a pyrolysis reactor having a reaction zone composed of ceramic material, for example. A pyrolysis reactor which is suitable for the process of the present invention is exemplified in U.S. Pat. No. 4,973,777. The pyrolysis of acrylonitrile, in the presence or absence of an inert gas, is advantageous at a temperature within the range from 900 to 1100° C. and with a residence time of less than 1 s. Preference is given to residence times of $\leq 0.2$ s, especially $\leq 0.1$ s. When the residence time is 0.1 sec, the acetylene yield is 34.2% and the hydrocyanic acid yield 53.4%. The process of the present invention can be carried out at atmospheric pressure or under superatmospheric pressure, but in both cases advantageously without catalysis.

The process of the present invention is surprising in that it achieves acrylonitrile pyrolysis according to the above equation at a temperature as low as about 1000° C. with an acrylonitrile conversion of >60%.

The process of the present invention is advantageously carried out continuously in a tubular reactor with the aforementioned residence times of less than 1 s; the resulting pyrolysis gases are quenched in a liquid immediately on leaving the high temperature zone. Preference is given in particular to a procedure wherein the gaseous reaction products of the pyrolysis are quenched down to less than 100° C. immediately, advantageously within seconds, preferably within $\leq 1$ s, of leaving the pyrolysis zone. The cooling medium is advantageously an inert liquid which preferentially absorbs the hydrocyanic acid from the acetylene/hydrocyanic acid mixture; an example of a suitable cooling medium is a mixture of aqueous NaOH solution and dimethylformamide.

The quenching can also be effected according to customary processes as described, for example, for the oil quench acetylene process (Ullmann's, Encyclopedia of Industrial Chemistry, 5th ed.—1985, Vol. A1, p. 107ff) and the Andrussow or the BMA hydrocyanic acid production process (Ullmann's, Encyclopedia of Industrial Chemistry, 5th ed.—1987, Vol. A8, p. 161ff).

One advantage of the process of the present invention over acetylene production from methane or natural gas is that the pyrolysis of acrylonitrile under the conditions described produces virtually no carbon black.

EXAMPLE

An upright reaction tube (diameter 4 cm, length 25 cm) was packed with ceramic rings (diameter 4 mm, length 4 mm). The reaction zone (length 2 cm, diameter 4 cm) was heated with a glowing metal strip to a temperature of about 1000° C. By means of a pump, 15.7 ml/h (12.65 g/h) of acrylonitrile were introduced into a vaporizer zone and mixed therein with 158 l/h of carrier gas (nitrogen) to form a gas mixture having an acrylonitrile content of 3.27% by volume. This gas mixture was passed through the reaction zone with a residence time in the reaction zone of 0.1 s.

Directly downstream of the reaction zone, the hot gases were quenched with a cold aqueous sodium hydroxide solution/DMF mixture. In the process, the hydrocyanic acid was absorbed. The remaining gas was subsequently dried and passed through gas collection tubes. The acetylene quantity determined by gas analysis was 1.12% by volume, corresponding to an acetylene yield of 34.2%. The titrimetrically determined amount of hydrocyanic acid after a run of 34 min was 1.95 g, corresponding to a yield of 53.4%.

We claim:

1. A process for preparing acetylene and hydrocyanic acid, which comprises pyrolyzing acrylonitrile in a reactor, wherein gaseous reaction products of the pyrolysis are quenched down to less than 100° C. immediately on leaving a pyrolysis zone of the reactor.

2. The process of claim 1, wherein the gaseous reaction products of the pyrolysis are quenched within seconds of leaving the pyrolysis zone.

3. The process of claim 2, wherein the reaction products are quenched in a liquid phase.

4. The process of claim 2, wherein the reaction products are quenched in a liquid phase by means of an inert liquid.

5. The process of claim 1, wherein the pyrolizing of the acrylonitrile is effected at 900–1100° C. with a residence time of less than 1 s in the presence or absence of an inert gas.

6. The process of claim 1, wherein the pyrolizing is effected continuously in a tubular reactor.

7. The process of in claim 1, wherein the gaseous reaction products of the pyrolysis are quenched within less than or equal to one second of leaving the pyrolysis zone.

8. The process of claim 7, wherein the reaction products are quenched in a liquid phase by means of an inert liquid.

9. The process of claim 7, wherein the pyrolizing of the acrylonitrile is effected at 900–1100° C. with a residence time of less than 1 s in the presence or absence of an inert gas.

10. The process of claim 9, wherein the pyrolizing is effected continuously in a tubular reactor.

* * * * *